US012029492B2

(12) United States Patent
Larin et al.

(10) Patent No.: US 12,029,492 B2
(45) Date of Patent: Jul. 9, 2024

(54) SYSTEM AND METHOD FOR MEASURING INTRAOCULAR PRESSURE AND OCULAR TISSUE BIOMECHANICAL PROPERTIES

(71) Applicant: University of Houston System, Houston, TX (US)

(72) Inventors: Kirill V. Larin, Friendswood, TX (US); Manmohan Singh, Houston, TX (US); Jiasong Li, Pearland, TX (US); Zhaolong Han, Shanghai (CN); Michael D. Twa, Birmingham, AL (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 18/072,838

(22) Filed: Dec. 1, 2022

(65) Prior Publication Data

US 2023/0210371 A1 Jul. 6, 2023

Related U.S. Application Data

(63) Continuation of application No. 16/228,979, filed on Dec. 21, 2018, now Pat. No. 11,553,839, which is a
(Continued)

(51) Int. Cl.
*A61B 3/16* (2006.01)
*A61B 3/10* (2006.01)
(Continued)

(52) U.S. Cl.
CPC .............. *A61B 3/165* (2013.01); *A61B 3/102* (2013.01); *A61B 3/18* (2013.01); *A61B 5/0066* (2013.01);
(Continued)

(58) Field of Classification Search
CPC ........... A61B 3/165; A61B 3/102; A61B 3/18; A61B 3/107; A61B 5/0066; A61B 5/7246;
(Continued)

(56) References Cited

U.S. PATENT DOCUMENTS 5,042,483 A * 8/1991 Nishio .................... A61B 3/165
600/401
2009/0015842 A1* 1/2009 Leitgeb .............. G01B 9/02003
356/456
(Continued)

OTHER PUBLICATIONS

Manapuram RK, Aglyamov SR, Monediado FM, Mashiatulla M, Li J, Emelianov SY, Larin KV. In vivo estimation of elastic wave parameters using phase-stabilized swept source optical coherence elastography. J Biomed Opt. Oct. 2012;17(10):100501. doi: 10.1117/1.JBO.17.10.100501. PMID: 23223976; (Year: 2012).*
(Continued)

*Primary Examiner* — Uzma Alam
*Assistant Examiner* — Jonathon Cook
(74) *Attorney, Agent, or Firm* — Jackson Walker LLP (57) ABSTRACT

Provided herein are systems and methods to measure the intraocular pressure, ocular tissue geometry and the biomechanical properties of an ocular tissue, such as an eye-globe or cornea, in one instrument. The system is an optical coherence tomography subsystem and an applanation tonometer subsystem housed as one instrument and interfaced with a computer for at least data processing and image display. The system utilizes an air-puff and a focused micro air-pulse to induce deformation and applanation and displacement in the ocular tissue. Pressure profiles of the air puff with applanation times are utilized to measure intraocular pressure. Temporal profiles of displacement and/or spatio-temporal profiles of a displacement-generated elastic wave are analyzed to calculate biomechanical properties.

9 Claims, 6 Drawing Sheets

Related U.S. Application Data continuation of application No. PCT/US2017/038799, filed on Jun. 22, 2017.

(60) Provisional application No. 62/353,398, filed on Jun. 22, 2016.

(51) Int. Cl.
  *A61B 3/107* (2006.01)
  *A61B 3/18* (2006.01)
  *A61B 5/00* (2006.01)

(52) U.S. Cl.
  CPC .......... *A61B 5/7246* (2013.01); *A61B 5/7289* (2013.01); *A61B 3/107* (2013.01)

(58) Field of Classification Search
  CPC .............. A61B 5/7289; G01B 9/02029; G01B 9/02031; G01B 9/02091; G01B 9/02002; G01B 9/02004
  See application file for complete search history.

(56) References Cited

U.S. PATENT DOCUMENTS

| | | | | |
|---|---|---|---|---|
| 2010/0238408 | A1* | 9/2010 | Roberts | A61B 3/165 702/50 |
| 2013/0211285 | A1* | 8/2013 | Fuller | A61B 5/031 600/561 |
| 2014/0114145 | A1* | 4/2014 | Wang | A61B 3/165 600/301 |
| 2015/0109621 | A1* | 4/2015 | Huber | G01B 9/02043 356/479 |
| 2016/0341539 | A1* | 11/2016 | Adie | G01B 9/02091 |

OTHER PUBLICATIONS

David Alonso-Caneiro, Karol Karnowski, Bartlomiej J. Kaluzny, Andrzej Kowalczyk, and Maciej Wojtkowski, "Assessment of corneal dynamics with high-speed swept source Optical Coherence Tomography combined with an air puff system," Opt. Express 19, 14188-14199 (Year: 2011).*

T. -M. Nguyen et al., "Shear wave elastography of ex vivo human corneas using phase-sensitive optical coherence tomography," 2014 IEEE International Ultrasonics Symposium, Chicago, IL, USA, 2014, pp. 217-220, doi: 10.1109/ULTSYM.2014.0055. (Year: 2014).*

Wang RK, Nuttall AL. Phase-sensitive optical coherence tomography imaging of the tissue motion within the organ of Corti at a subnanometer scale: a preliminary study. J Biomed Opt. Sep. 2010-Oct. 15(5):056005. doi: 10.1117/1.3486543. PMID: 21054099; PMCID: PMC2948044. (Year: 2010).*

R. Huber, M. Wojtkowski, and J. G. Fujimoto, "Fourier Domain Mode Locking (FDML): A new laser operating regime and applications for optical coherence tomography," Opt. Express 14, 3225-3237 (2006) (Year: 2006).*

Twa MD, Li J, Vantipalli S, Singh M, Aglyamov S, Emelianov S, Larin KV. Spatial characterization of corneal biomechanical properties with optical coherence elastography after UV cross-linking. Biomed Opt Express. Apr. 4, 2014;5(5):1419-27. doi: 10.1364/BOE. 5.001419. PMID: 24877005; PMCID: PMC4026912 (Year: 2014).*

\* cited by examiner

SYSTEM AND METHOD FOR MEASURING INTRAOCULAR PRESSURE AND OCULAR TISSUE BIOMECHANICAL PROPERTIES

CROSS-REFERENCE TO RELATED APPLICATIONS

This application is a continuation of and claims priority to U.S. patent application Ser. No. 16/228,979 filed Dec. 21, 2018, which is a continuation under 35 U.S.C. § 120 of international patent application PCT/US2017/038799, filed Jun. 22, 2017 which claims benefit of priority under 35 U.S.C. § 119(e) of provisional application U.S. Ser. No. 62/353,398, filed Jun. 22, 2016, the entirety of each of which are hereby incorporated by reference.

GOVERNMENT SUPPORT CLAUSE

This invention was made with government support under grant numbers 1R01EY022362 and P30EY07551 awarded by the National Institutes of Health. The government has certain rights in the invention.

BACKGROUND OF THE INVENTION

Field of the Invention

The present invention generally relates to the field of eye care systems and methods of use. More specifically, the present invention relates to a non-contact technique of measuring the intraocular pressure (IOP) and geometry of the eye-globe with optical coherence tomography (OCT) and measuring biomechanical properties of ocular tissues using optical coherence elastography (OCE) with a single device.

Description of the Related Art

Current clinical tools provide critical information about ocular health such as intraocular pressure (IOP). Noncontact applanation tonometry (NAT) is one of the most common screening tools for ocular diseases, most notably glaucoma, by measuring intraocular pressure (IOP) (1). In addition to IOP measurements, applanation studies have been performed to try to quantify corneal biomechanical properties for detecting degenerative diseases such as keratoconus (2). However, the large displacements induced by the air-puff prohibit local assessment of corneal biomechanical properties (3) and cause nonlinear biomechanical behaviors (4). Moreover, biomechanical measurements of the cornea are confounded by other parameters, such as IOP5,6 and central corneal thickness (CCT).5,7 Thus, providing an accurate measurement of corneal mechanical parameters (e.g., Young's modulus) is not straightforward, let alone based on applanation measurements. Nevertheless, commercially available noncontact tonometers, e.g., the ocular response analyzer and CorVis ST, can distinguish between healthy and keratoconic corneas (8), but there are conflicting results on their ability to detect corneal biomechanical changes due to therapeutic interventions such as corneal collagen cross-linking (8,9). Therefore, it may not be entirely possible to separate the effects of corneal geometry, IOP, and corneal biomechanical properties from their respective individual measurements for corrections.

Optical coherence tomography (OCT) is a versatile and non-invasive imaging technique that provides depth-resolved images with micrometer-scale resolution (10). The biomechanical properties of tissues can be measured using the elastographic functional extension of OCT, termed optical coherence elastography (OCE) (11,12,13). While the OCT structural image has a resolution on the scale of micrometers, phase-sensitive OCT has the capability for subnanometer displacement sensitivity (14), which is crucial for ultrasensitive elastographic measurements (15). Ultrasound elastography and magnetic resonance elastography are clinically available elastographic techniques, but are not well-suited for small and thin tissues such as the cornea and the sclera, due to their relatively lower spatial resolution, poorer displacement sensitivities and need for contact-based excitation or coupling medium.

Therefore, there is a recognized need for a single instrument and noncontact imaging system that can accurately measure these parameters in a subject. Particularly the prior art is deficient in an imaging device, system, method, and/or technique to accurately measure intraocular pressure and biomechanical properties of ocular tissues, including corneal, retinal, or scleral tissues. The present invention fulfills this long-standing need and desire in the art.

SUMMARY OF THE INVENTION

The present invention is directed to a system for measuring intraocular pressure, ocular tissue geometry and biomechanical properties of an ocular tissue. The system comprises, in one instrument, an optical coherence tomography subsystem and an applanation tonometer subsystem in electronic communication with the optical coherence tomography subsystem. The present invention is directed to a related system that further comprises a housing containing the subsystems, a computer comprising at least a memory, a processor, a digitizer, a display, and at least one network connection and an interface that is in electronic communication with said subsystems and with the computer.

The present invention also is directed to a method for measuring intraocular pressure, ocular tissue geometry and biomechanical properties in an ocular tissue in one instrument. In this method the ocular tissue of an eye globe is scanned with a laser source in the optical coherence tomography subsystem described herein and optical coherence tomography images are obtained. The intraocular pressure of the eye globe is calculated via the applanation tonometer subsystem and the geometry of the ocular tissue is measured based on the optical coherence tomography images. The biomechanical properties of the ocular tissue are quantified via the optical coherence tomography subsystem. The present invention is directed to a related method further comprising a step in which one or more images obtained during the scan are displayed. The present invention is directed to another related method further comprising a step in which one or more abnormalities in the ocular tissue based on the calculated intraocular pressure, an imaged ocular tissue geometry and the measured biomechanical properties is identified.

The present invention is directed further to an applanation-optical coherence elastography (Appl-OCE) system for measuring intraocular pressure, an ocular geometry and biomechanical properties in an eye of a subject. The system comprises operably linked components. The system components include a scanning laser source and a scanner operably linked to a scanner driver configured to scan the eye with radiation delivered from the laser source. The system components include an air-puff generator configured to deliver an air-puff of a force sufficient to deform and applanate a cornea of the eye and an air-pulse generator configured to deliver a focused micro air-pulse sufficient to generate a localized displacement or an elastic wave within the eye. A computer comprises at least a memory, a processor, a digitizer, a display, and at least one network connection and an interface in electronic communication with the system components. The present invention is directed to a related applanation-optical coherence elastography (Appl-OCE) system that further comprises a housing for the components.

The present invention is directed further still to a method for determining the health of an eye in a subject. In the method, the eye of the subject is scanned with the scanning laser source and the scanner of the applanation-optical coherence elastography (Appl-OCE) system described herein. The air-puff and the focused micro air-pulse, as described in the Appl-OCE system, are delivered to the eye. Images of the eye processed during the scanning and/or delivering steps are displayed. An intraocular pressure of the eye is measured from data obtained after delivering the air-puff and one or more biomechanical properties are measured from data obtained after delivering the focused micro air-pulse to the eye. The intraocular pressure, ocular tissue geometry and the one or more biomechanical properties are analyzed for pathophysiological abnormalities, thereby determining the health of the eye.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the present invention, there is provided a system for measuring intraocular pressure, ocular tissue geometry and biomechanical properties of an ocular tissue, comprising, in one instrument, an optical coherence tomography subsystem; and an applanation tonometer subsystem in electronic communication with the optical coherence tomography subsystem. Further to this embodiment the system may comprise a housing containing the subsystems; a computer comprising at least a memory, a processor, a digitizer, a display, and at least one network connection; and an interface in electronic communication with the subsystems and with the computer. In this further embodiment the computer may be configured to control the subsystems, to process data received from the subsystems, to generate one or more images from processed data, and to display the one or more images. In both embodiments the ocular tissue may comprise an in vivo or an ex vivo eye-globe, an in vivo or an ex vivo corneal tissue, or an ocular tissue mimic.

In one aspect of both embodiments, the optical coherence tomography subsystem may comprise means for scanning the ocular tissue, means for delivering an air-puff to the ocular tissue and means for delivering a focused micro air-pulse to the ocular tissue. In this aspect the means for scanning the ocular tissue may comprise, in electronic communication, a scanning laser source configured to operate at about 1260 nm to about 1370 nm, a resonant scanner configured to scan a laser beam emitted by the scanning laser source across the ocular tissue and a scanner driver configured to move the resonant scanner over the ocular tissue with operator-configurable scanning distance and phase. Also in this aspect, the means for delivering the air-puff to the ocular tissue may comprise, in combination, a rotary solenoid and a plunger configured to deliver the air-puff with a force sufficient to deform the ocular tissue. In addition, the means for delivering the air-pulse to the ocular tissue may comprise, in electronic communication, an air-pulse supply, an air-pulse controller and an electronically controlled pneumatic solenoid configured to produce the focused micro air-pulse from the air-pulse supply.

In another aspect of both embodiments the applanation tonometer subsystem may comprise means for delivering an air-puff to the ocular tissue, means for measuring a temporal pressure profile from deformation and applanation of the ocular tissue from the air-puff delivered thereto and means for calculating an intraocular pressure from the temporal pressure profile and imaged ocular tissue deformation and applanation. In this aspect the means for measuring the temporal pressure profile of the ocular tissue may be a pressure transducer configured to measure an air-puff pressure at a plurality of time points during deformation and applanation of the ocular tissue. Also the means for calculating the intraocular pressure may comprise software configured to correlate the times of applanation of the ocular tissue with a temporal pressure profile and to apply corrections as needed.

In another embodiment of the present invention there is provided a method for measuring intraocular pressure, ocular tissue geometry and biomechanical properties of an ocular tissue in one instrument, comprising scanning the ocular tissue of an eye globe with a laser source in the optical coherence tomography subsystem as described supra; obtaining optical coherence tomography images; calculating the intraocular pressure of the eye globe via the applanation tonometer subsystem; measuring the geometry of the ocular tissue based on the optical coherence tomography images; and quantifying the biomechanical properties of the ocular tissue via the optical coherence tomography subsystem. Further to this embodiment the method may comprise displaying one or more images obtained during the scanning step. In another further embodiment the method may comprise identifying one or more abnormalities in the ocular tissue based on the calculated intraocular pressure, an imaged ocular tissue geometry and the measured biomechanical properties. In all embodiments biomechanical properties comprise axial displacement, relaxation rate, relaxation process, frequency of relaxation process, natural frequency, spectral properties, Young's modulus, elasticity, viscosity, maximum deformation, corneal thickness, corneal curvature, inward velocity, outward velocity, maximum inward curvature, damping or a combination thereof.

In all embodiments the scanning step may comprise delivering to the ocular tissue, via the laser source, radiation with a wavelength from about 1260 nm to about 1370 nm and imaging the ocular tissue.

Also in all embodiments the calculating step may comprise delivering an air-puff with a force sufficient to induce a deformation and applanation in the optical tissue, measuring a pressure of the air-puff at a plurality of time points during deformation and applanation of the ocular tissue as a temporal pressure profile and correlating the pressures measured at times of applanation of the ocular tissue with the measured temporal pressure profile. Further to the calculating step the method may comprise displaying images of the deformation and applanation of the ocular tissue. Further still the method may comprise calibrating intraocular pressure by integrating an ocular geometry into the images and calculations of the deformation and applanation.

In addition in all embodiments the quantifying step may comprise delivering a focused micro air-pulse to the ocular tissue to induce a low amplitude displacement therein, measuring the low amplitude displacement at a point of excitation or at multiple points of excitation at different spatial positions to detect an air-pulse induced elastic wave, and quantifying, as the biomechanical properties, one or more characteristics of the displacement of the ocular tissue or of the elastic wave or a combination thereof obtained from the profiles and correcting the measured biomechanical properties utilizing the geometry of the ocular tissue. Further to this embodiment the quantifying step may comprise displaying images of the displacement of the ocular tissue.

In yet another embodiment of the present invention there is provided an applanation-optical coherence elastography (Appl-OCE) system for measuring intraocular pressure, an ocular tissue geometry and biomechanical properties in an eye of a subject, comprising, as operably linked components, a scanning laser source; a scanner operably linked to a scanner driver configured to scan the eye with radiation delivered from the laser source; an air-puff generator configured to deliver an air-puff of a force sufficient to deform and applanate a cornea of the eye; an air-pulse generator configured to deliver a focused micro air-pulse sufficient to generate a local displacement or an elastic wave within the eye; and a computer comprising at least a memory, a processor, a digitizer, a display, and at least one network connection and an interface in electronic communication with the system components. Further to this embodiment the Appl-OCE system may comprise a housing.

In both embodiments the laser source may be a scanning laser source configured to operate at about 1266 nm to about 1366 nm. Also in both embodiments the air-puff generator may comprise, in combination, a rotary solenoid and a plunger. In addition the air-pulse generator may comprise an air-pulse supply, an electronically controlled pneumatic solenoid and an air-pulse controller operably-linked to and configured to produce a focused micro air-pulse from the air-pulse supply.

In all embodiments the computer may be configured to enable processor-executable instructions to produce and display images of the eye from displacement data obtained during the scan, the focused micro air-pulse, and the air-puff, to measure a temporal pressure profile from deformation and applanation data of the cornea from the air-puff, to calculate an intraocular pressure from the measured displacement data and measured air-puff temporal pressure profile, to generate a temporal profile of a displacement in the ocular tissue induced by the focused micro air-pulse, to generate spatiotemporal profiles of an elastic wave produced within the ocular tissue in response to the air-pulse induced displacement thereof, and to quantify one or more characteristics of the air-pulse induced displacement or elastic wave as one or more biomechanical properties.

In yet another embodiment of the present invention there is provided a method for determining the health of an eye in a subject, comprising the steps of scanning the eye of the subject with the scanning laser source and the scanner of the applanation-optical coherence elastography (Appl-OCE) system as described supra; delivering to the eye the air-puff and the focused micro air-pulse; displaying images of the eye processed during the scanning or delivering steps or combination thereof; measuring an intraocular pressure of the eye from data obtained after delivering the air-puff; measuring one or more biomechanical properties from data obtained after delivering the focused micro air-pulse to the eye; and analyzing the intraocular pressure, ocular tissue geometry and one or more biomechanical properties for pathophysiological abnormalities, thereby determining the health of the eye.

In this embodiment the step of measuring an intraocular pressure may comprise measuring a pressure of the air-puff at a plurality of time points during deformation and applanation of the cornea and correlating the pressures measured at times of applanation of the cornea with a measured pressure profile thereof. Further to this measuring step the method may comprise calibrating intraocular pressure by integrating an ocular geometry into images and calculations of the deformation and applanation after delivery of the air-puff and calculating ocular tissue biomechanical properties utilizing ocular tissue geometry after delivery of the focused micro air-pulse.

Also in this embodiment the step of measuring one or more biomechanical properties step may comprise calculating at a plurality of time points a temporal profile of the displacement in the eye after delivery of the air-pulse; calculating at a plurality of time points spatio-temporal profiles of an elastic wave generated within the eye in response to the displacement thereof, or a combination thereof, and quantifying, as the biomechanical properties, one or more characteristics of the displacement of the eye or of the elastic wave or a combination thereof obtained from the profiles.

In addition in this embodiment the biomechanical properties may comprise axial displacement, relaxation rate, relaxation process, frequency of relaxation process, natural frequency, spectral properties, Young's modulus, shear modulus, elasticity, viscosity, shear viscosity, maximum deformation, corneal thickness, corneal curvature, inward velocity, outward velocity, maximum inward curvature, damping or a combination thereof.

Provided herein are optical imaging systems configured to measure, in ocular tissue, the intraocular pressure, to quantify biomechanical properties of the ocular tissue and to measure ocular geometry, such as of the cornea, using a single instrument or device. Particularly, the single instrument imaging system is an ultrafast applanation optical coherence elastography (Appl-OCE) system that comprises a phase-sensitive swept source optical coherence tomography (Phs-SS-OCT) subsystem that provides high-resolution and depth-resolved images of the target ocular tissue and an applanation tonometer subsystem configured to visualize corneal dynamics during noncontact applanation tonometry and to directly measure a focused micro air-pulse induced displacement or a focused micro air-pulse induced elastic wave propagation as described herein. Representative examples of an ocular tissue are, the eye, eye-globe and/or cornea of a subject, an ex vivo eye-globe, an ex vivo corneal sample, or any optical tissue mimic.

Applanation Optical Coherence Elastography (Appl-OCE) System

The Applanation Optical Coherence Elastography (Appl-OCE) system 100 comprises, as operably linked components a Phase-Sensitive Swept Source Optical Coherence Tomography (PhS-SSOCT) subsystem for optical coherence elastography (OCE) and an applanation tonometer subsystem (FIG. 1) Generally, the PhS-SSOCT subsystem includes, but is not limited to, an optical coherence tomography device with an elastographic functional extension or optical coherence elastography (OCE) functionality, an air-puff delivering device, an air-pulse, such as a focused micro air-pulse, delivering device, and a computer. Alternatively, the micro focused air-pulse delivering device may be part of the elastographic functional extension. The applanation tonometer subsystem generally includes, but is not limited to, means for generating a large force air-puff, a pressure transducer and software to calculate and transmit data received from delivery of the large force air-puff.

Figure 1:
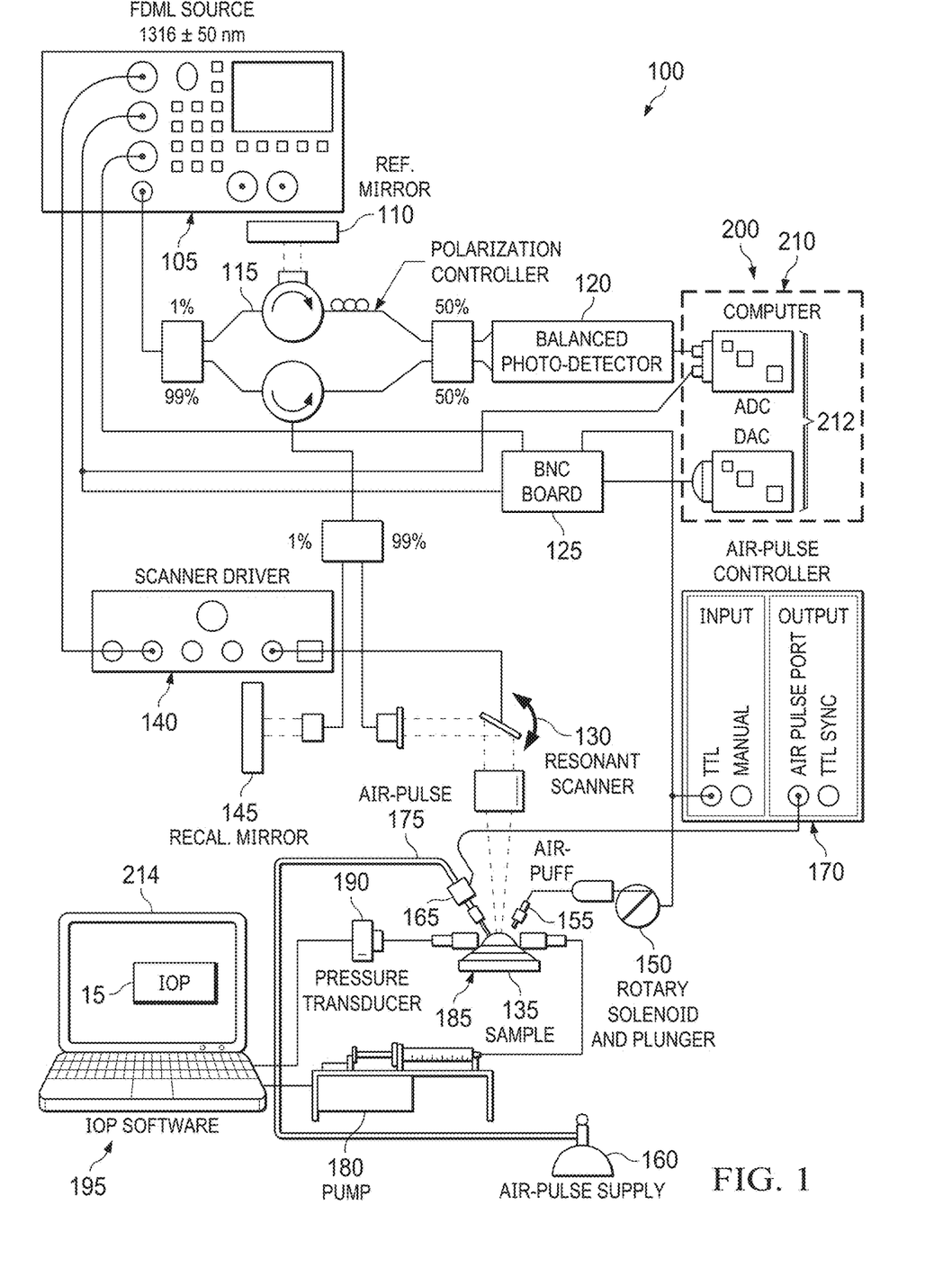
FIG. 1 is a schematic of the Applanation Optical Coherence Elastography (Appl-OCE) imaging system that combines, as a subsystem, a phase-sensitive Swept Source Optical Coherence Tomography (PhS-SSOCT) system for optical coherence elastography (OCE) and an OCT-based applanation tonometer subsystem.

The optical coherence tomography device comprises, in an operably-linked relationship, a Fourier Domain Mode Locked (FDML) scanning laser source 105 operating to scan a laser beam at white light, near-infrared or infrared wavelengths, for example, at about 1260 to about 1370 nm, preferably about 1266 nm to about 1366 nm or more preferably about 1316 nm, a reference mirror 110, a polarization controller 115, a balanced photodetector 120, a Bayonet Neill-Concelman (BNC) board 125, a resonant scanner 130 configured to scan the sample 135, such as an ocular tissue, the eye and/or cornea of a subject, an ex vivo eye-globe, an ex vivo corneal sample, or any optical tissue mimic, a resonant scanner driver 140 operably linked to the laser source and to the resonant scanner, and a recalibration mirror 145. The scanner driver is operator-configurable for scanning distance and phase when moving the resonant scanner.

An air-puff generator, configured to generate a air puff for imaging of the optical tissue, comprises a solenoid and plunger combination 150 connected to the amplifier and configured to fluidly deliver the air puff. The air-puff is delivered at 155. The air-pulse generator comprises an air-pulse supply 160 and an electronically controlled pneumatic solenoid 165 in electronic connection with an air pulse controller 170. The air-pulse is delivered at 175.

The applanation tonometer subsystem comprises an air pump 180 configured to generate a large force air-puff delivered to the sample at 185. A pressure transducer 190 receives data comprising the inward and outward deformations and the two points of applanation of the sample and via IOP software 195 calculates the pressure profile.

A housing (not shown) contains all the components of the subsystem. An electronic interface 200 connects to a computer 210. The computer is configured for controlling the system, data and image processing including a digitizer 212 for analog-to-digital and digital-to-analog converters, and image display 214.

Also provided are ultra-fast methods for quantifying or measuring intraocular pressure and/or performing quantitative elastographic evaluation of the cornea using the noncontact Appl-OCE system. Generally, a large force air-puff is delivered to deform and applanate the cornea and optical coherence tomography images are taken. The air-puff induces a deformation in the ocular tissue, causing it to deform inwards. The entire dynamic deformation is imaged with micrometer-scale spatial resolution and microsecond-scale temporal resolution and integrates ocular geometry into the calculations for calibration of the intraocular pressure. On the inwards and outwards processes, there is a point at which the cornea is flat or applanated. By measuring the temporal pressure profile of the air-puff, the applanation times are correlated with an air puff pressure. The intraocular pressure can then be estimated under the simple assumption that the forces on the anterior surface of the cornea (i.e., air-puff) and posterior surface of the cornea (i.e., IOP) are equal when the cornea is applanated (i.e., flat).

To measure the elasticity or stiffness of the cornea with the Appl-OCE system, a focused micro air-pulse induces a low amplitude displacement (micro to nanometer-scale) in the cornea that then propagates as an elastic wave. The phase-resolved measurements provide the spatio-temporal profiles of the elastic wave or temporal profile of the air-pulse induced displacement. These two parameters enable further quantification of the wave and displacement characteristics, for example, but not limited to, group velocity, phase velocity, dispersion, relaxation rate, and/or natural frequency, and subsequent ocular tissue stiffness, elasticity, shear modulus, viscosity, or shear viscosity or combinations thereof. Spectral analysis of the elastic wave and model-based viscoelasticity reconstruction then provides a depth-resolved elasticity characterization.

Thus, the present invention further provides a method for clinically evaluating the health of an eye and its tissues. The Appl-OCE system is useful to measure the biomechanical properties of the cornea in its natural resting state in the eye-globe with small displacements that minimize the effects of the corneal nonlinear biomechanical properties. Measuring the IOP and quantifying tissue material properties which are markers for ocular tissue health and integrity together enables one to ascertain whether abnormal measurements of either are due to a pathological IOP or other pathophysiological condition or to inherent tissue biomechanical properties. Particularly, the biomechanical properties are one or more of axial displacement, relaxation rate, relaxation process, frequency of the relaxation process, natural frequency, spectral properties, Young's modulus, shear modulus, elasticity, viscosity, shear viscosity, maximum deformation, corneal thickness, corneal curvature, inward velocity, outward velocity, maximum inward curvature, and damping.

The following examples are given for the purpose of illustrating various embodiments of the invention and are not meant to limit the present invention in any fashion.

Example 1

Materials and Methods

Agar Phantom Samples

Tissue-mimicking agar phantoms (Difco nutrient agar, Beckton, Dickinson and Company, Sparks, Md., USA) were used. Concentrations (w/w) of agar are 1%, 1.5% and 2%, n=3 of each concentration.

Porcine Eyes

Fresh porcine eyes (Sioux-Preme Packing Company, Sioux City, Iowa; n=3) are used. Extraneous tissues such as muscles are removed from the eye-globes and all measurements were taken within 24 h of enucleation. The whole eye-globes were placed in a home-built holder for artificial IOP control (17). During testing, the eye-globes are cannulated with two 23 G needles for an artificial IOP control. One needle was connected via tubing to a pressure transducer and the other needle was connected via tubing to a microinfusion pump.

Video

Video of noncontact applanation (Video 1) or elastic wave propagation (Video 2) was imaged at a frame rate of ~7.3 kHz.

Video 1, MP4, 6.5 MB, dx.doi.org/10.1117/1.JBO.22.2.020502.1; and

Video 2, MP4, 4 MB, dx.doi.org/10.1117/1.JBO.22.2.020502.2.

Example 2

Optical Imaging System

Phase-Sensitive Swept-Source Optical Coherence Tomography (PhS-SSOCT) Imaging Subsystem The phase-sensitive swept source Optical Coherence Tomography system (PhS-SSOCT) (see FIG. 1) imaging system utilizes a 4×buffered Fourier domain model locked (FDML) swept source laser with an A-scan or sweep rate of ~1.5 MHz, a central wavelength of ~1316 nm, a scan range of ~100 nm, an axial resolution of ~16 µm, a phase stability of ~14 nm, and a resonant scanner at ~7.3 kHz. The PhS-SSOCT optical imaging system is utilized to image the dynamic spatio-temporal deformation of the cornea in response to the air-puff and detect the nano to micrometer-scale displacements induced by the focused air-pulse. The PhS-SSOCT imaging system is controlled by a computer comprising at least a processor, memory, analog-to-digital (ADC) and digital-to-analog (DAC) converters, a display, and other requisite software and hardware to operate the system and at least one network connection.

Applanation Optical Coherence Elastography (Appl-OCE) System

The Applanation Optical Coherence Elastography imaging system (FIG. 1) comprises the PhS-SSOCT system and means for making intraocular pressure measurements, imaging the ocular tissue geometry, and measuring the air-pulse induced displacements, either at the excitation position or different spatial positions to detect the air-pulse induced elastic wave propagation. The Appl-OCE system utilizes the rotary solenoid and plunger to provide the large force air-puff during the applanation measurements. The Appl-OCE system utilizes a focused micro air-pulse excitation system (18) for the elastographic measurements.

Example 3

PhS-SSOCT Assessment of Elasticity of Optical Samples

Agar Phantom

Figure 2:
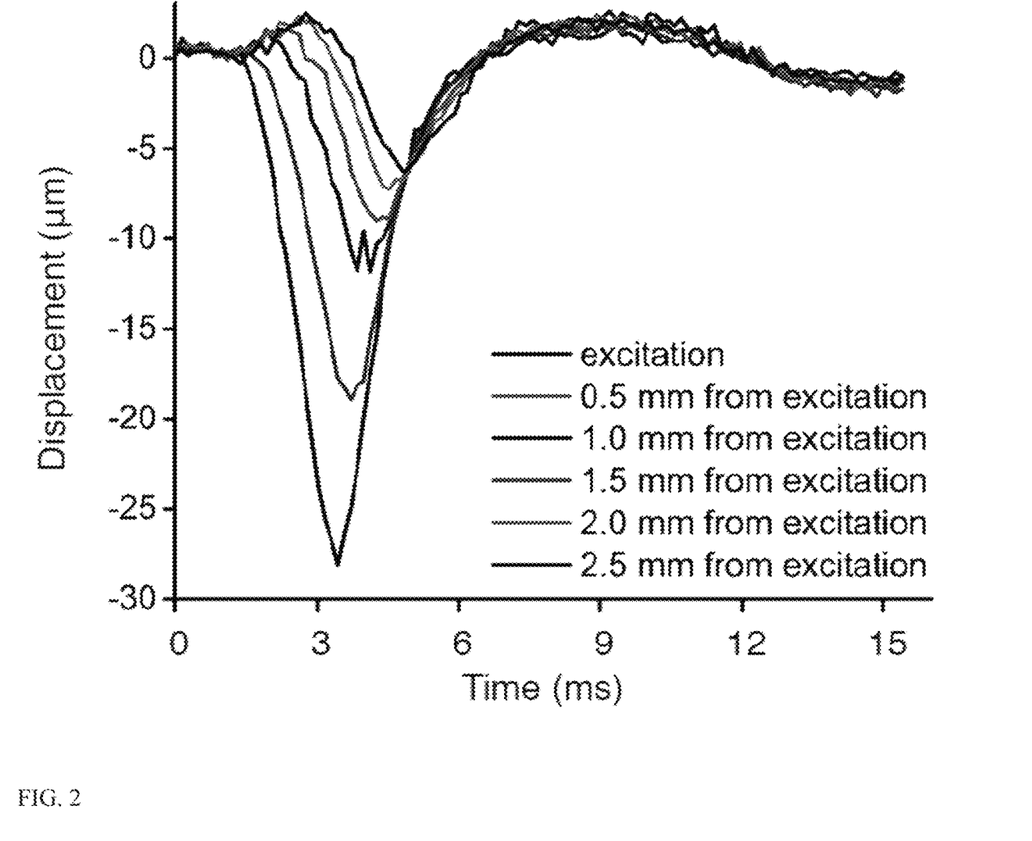
FIG. 2 depicts the temporal vertical displacement profiles of an elastic wave from the surface of a tissue-mimicking agar phantom at the indicated distances away from the excitation induced by the air-pulse.

The propagation of the air-pulse induced elastic wave in a tissue-mimicking agar phantom is illustrated in FIG. 2. The temporal vertical displacement profiles at the indicated distances are plotted. The distances are at about 0.5 mm, 1.0 mm, 1.5 mm, 2.0 mm and 2.5 mm away from the air-pulse excitation. The largest displacement at all the distance appears at the time of about 3 ms, and the displacement is fully recovered after about 6 ms for all the excitation distances. The wave propagation, attenuation, and dispersion can be observed from the shape of the profiles at the various distances and can be also be used to calculate biomechanical properties.

Figure 3:
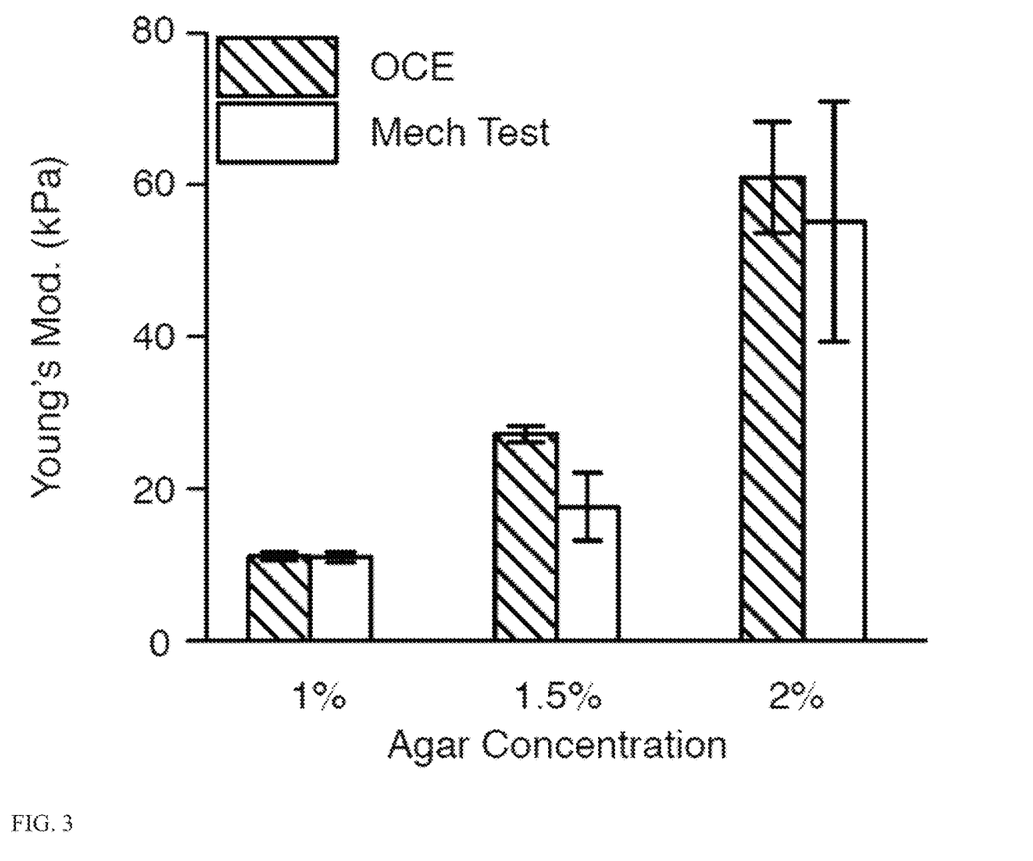
FIG. 3 shows the comparison of the stiffness for agar phantoms at various concentrations (1%, 1.5%, and 2% w/w, n=3 of each concertation) assessed by optical coherence elastography and as measured by the "gold standard" uniaxial mechanical compression testing.

In order to validate the optical coherence elastography technique, the stiffness of agar phantoms of various concentrations (1%, 1.5%, and 2% w/w, n=3 of each concertation) assessed by optical coherence elastography and measured by the "gold standard" uniaxial mechanical compression testing are compared. The Young's modulus as obtained by both methods of the phantoms is plotted in FIG. 3. The results show that the optical coherence elastography and uniaxial mechanical compression test generates comparable results at all three agar concentrations. Especially, at the agar concentration of 1%, the results from optical coherence elastography are very similar as the uniaxial mechanical compression test.

Example 4

Figure 4:
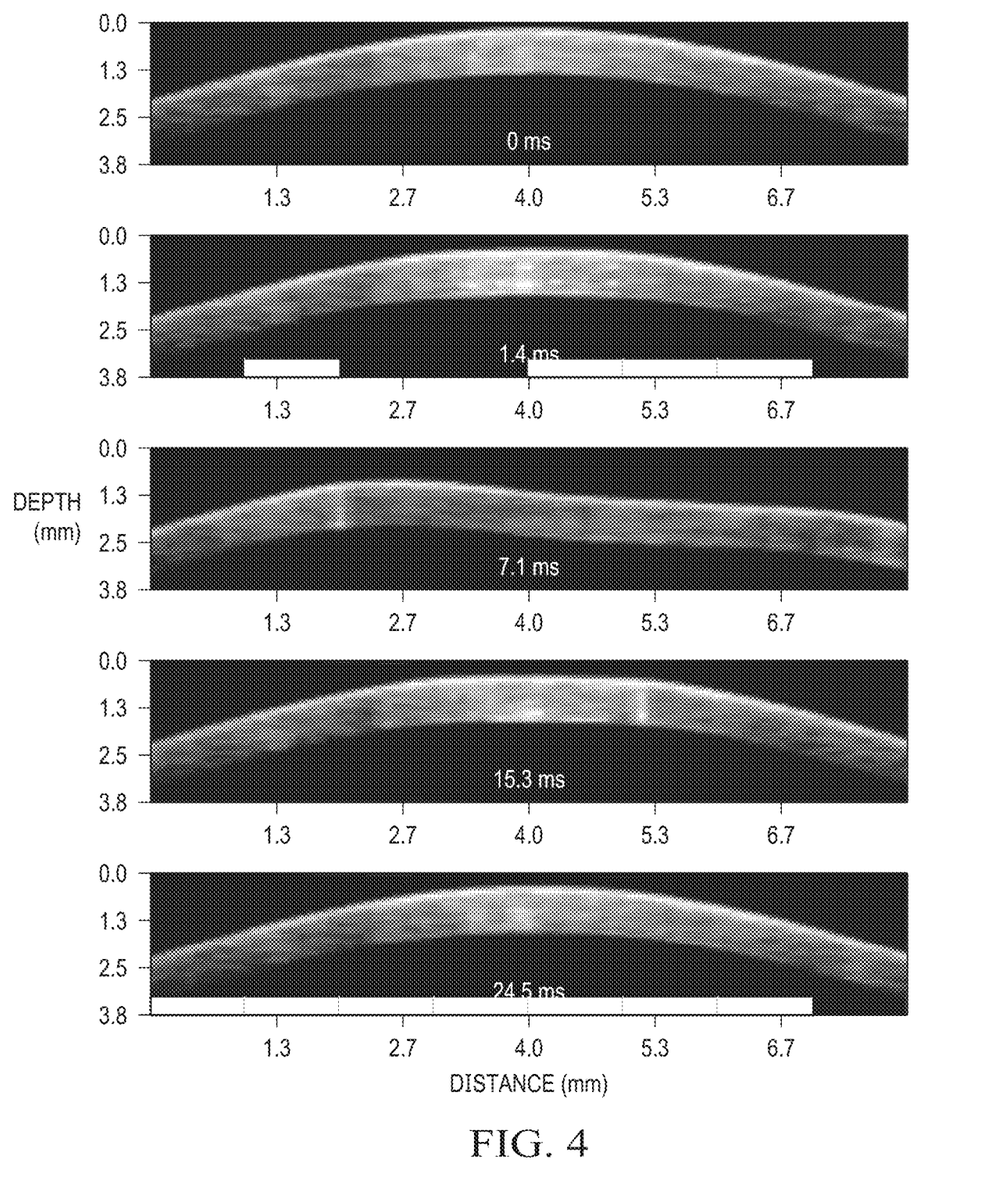
FIG. 4 shows the deformation of the cornea in response to the air-puff at an artificially controlled IOP of 10 mmHg. The images are taken at the time points of about 0 ms, 1.4 ms, 7.1 ms, 15.3 ms, and 24.5 ms after the air-puff excitation.

Appl-OCE Intraocular Pressure, Corneal Geometry and Biomechanical Measurements on an Ex Vivo Cornea The dynamic tissue responses to air-puff and micro air-pulse excitations are detected with the Appl-OCE system. During applanation, a large force air-puff was directed at the central region of the porcine cornea in situ in the whole eye-globe configuration, which was recorded by the OCT system with a frame rate of ~7.3 kHz as Video 1 (1000× slower than real-time) (FIG. 4). The total duration is approximately 25 ms. During the inward and outward deformations, there are two times when the cornea is applanated at 1.4 and 15.3 ms after excitation, respectively.

To calculate the intraocular pressure (IOP), it was assumed that the force on the anterior surface, i.e. the air-puff, and posterior surface, i.e. the IOP, of the cornea were equal at the times when the cornea was applanated. The time between applanation states were used to obtain the intraocular pressure from the air-puff pressure profile, which was measured by a pressure transducer. Measuring the intraocular pressure can also be accomplished by proper synchronization rather than the difference between the applanation times. The air-puff pressure profile can be adjusted to a suitable dynamic range for the target with or without a priori information. The dynamic range of pressure displayed in this document is not truly indicative of the detectable pressure range. Four applanation measurements were taken for each porcine sample at each IOP setting. To corroborate the results, IOP measurements were also made with a rebound tonometer (TonoVet, iCareUSA, North Carolina) immediately after the respective applanation measurements by the Appl-OCE system. Five measurements were made for each sample at each IOP by the rebound tonometer.

Figure 5:
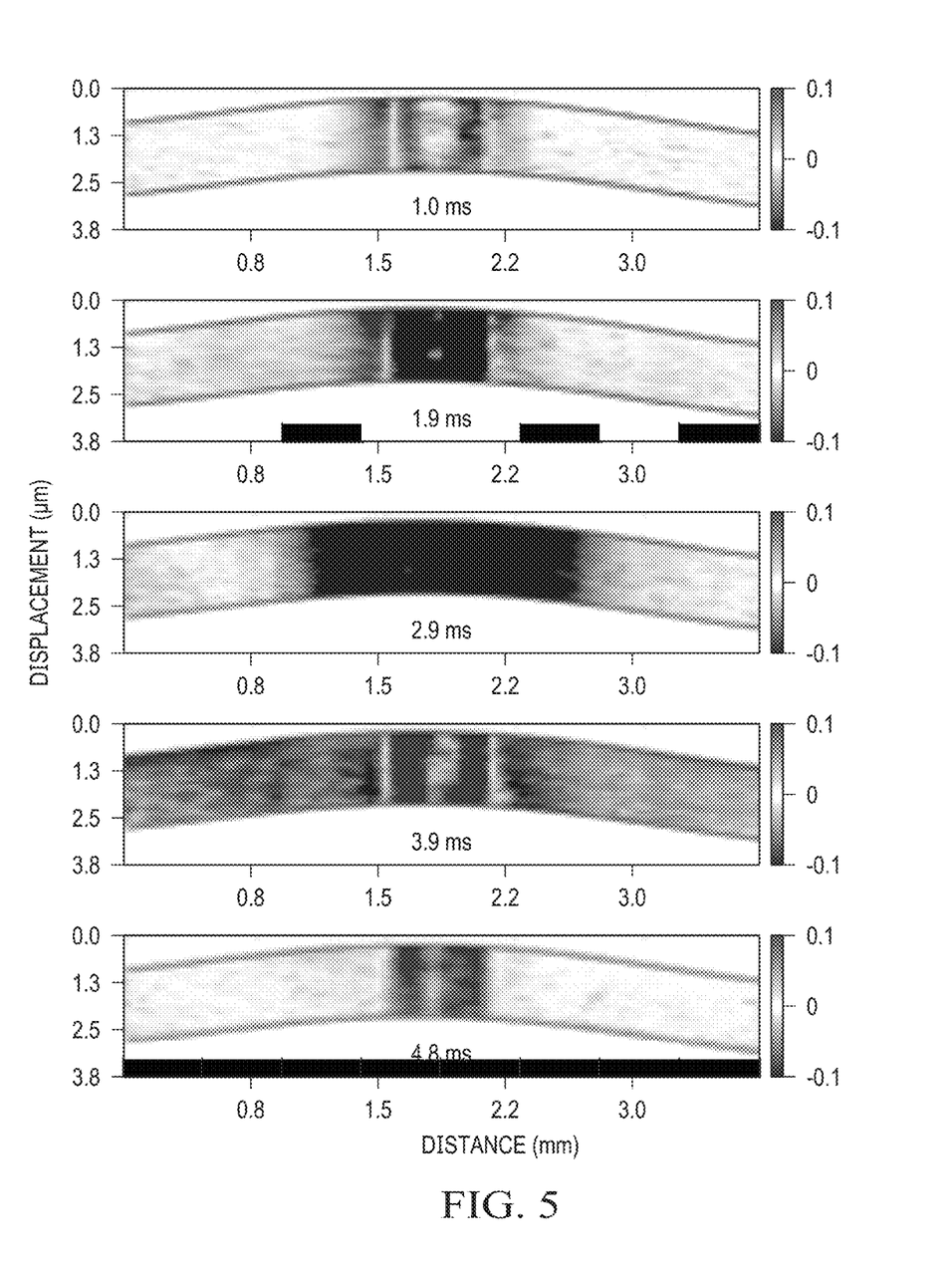
FIG. 5 shows the propagation of an air-pulse induced elastic wave in a corneal sample at an artificially controlled IOP of 10 mmHg. The images are taken at the time points of about 1.0 ms, 1.9 ms, 2.9 ms, 3.9 ms, and 4.8 ms after the air-pulse excitation.

After the applanation measurements, a focused micro air-pulse induced an elastic wave in the cornea, which was also detected by the same phase-sensitive OCT system as in FIG. 1. Briefly, the air-pulse induced a localized displacement, when then propagated transversely as an elastic wave, which was imaged by repeated B-scans. The number of A-scans in each B-scan was a multiple of four to ensure that each repeated A-scan at a given spatial position was from the same buffered sweep since the FDML laser utilized 4×buffering (21). The phase data was corrected to remove surface motion and refractive index mismatch artifacts, with the refractive index of the cornea as 1.376 (22, 23). Selected temporal frames from Video 2 (1000× slower than real-time) of the air-pulse induced elastic wave propagating across the porcine cornea at 10 mmHg IOP (FIG. 5). The dark regions near the apex are due to phase unwrapping errors, and these positions were not used for elasticity quantification. The elastic wave velocity was calculated by cross-correlation analysis and linear fitting of the temporal displacement profiles at different spatial positions in the linear scan region. Similar to the applanation measurements, four line measurements over the same apical region were taken for each sample for each IOP setting. The OCE measurements were taken along the nasal/temporal axis of each cornea to limit the effects of corneal mechanical anisotropy on the OCE measurements (24). The Young's modulus was estimated from the group velocity using the surface wave equation as described (16, 25).

Figure 6:
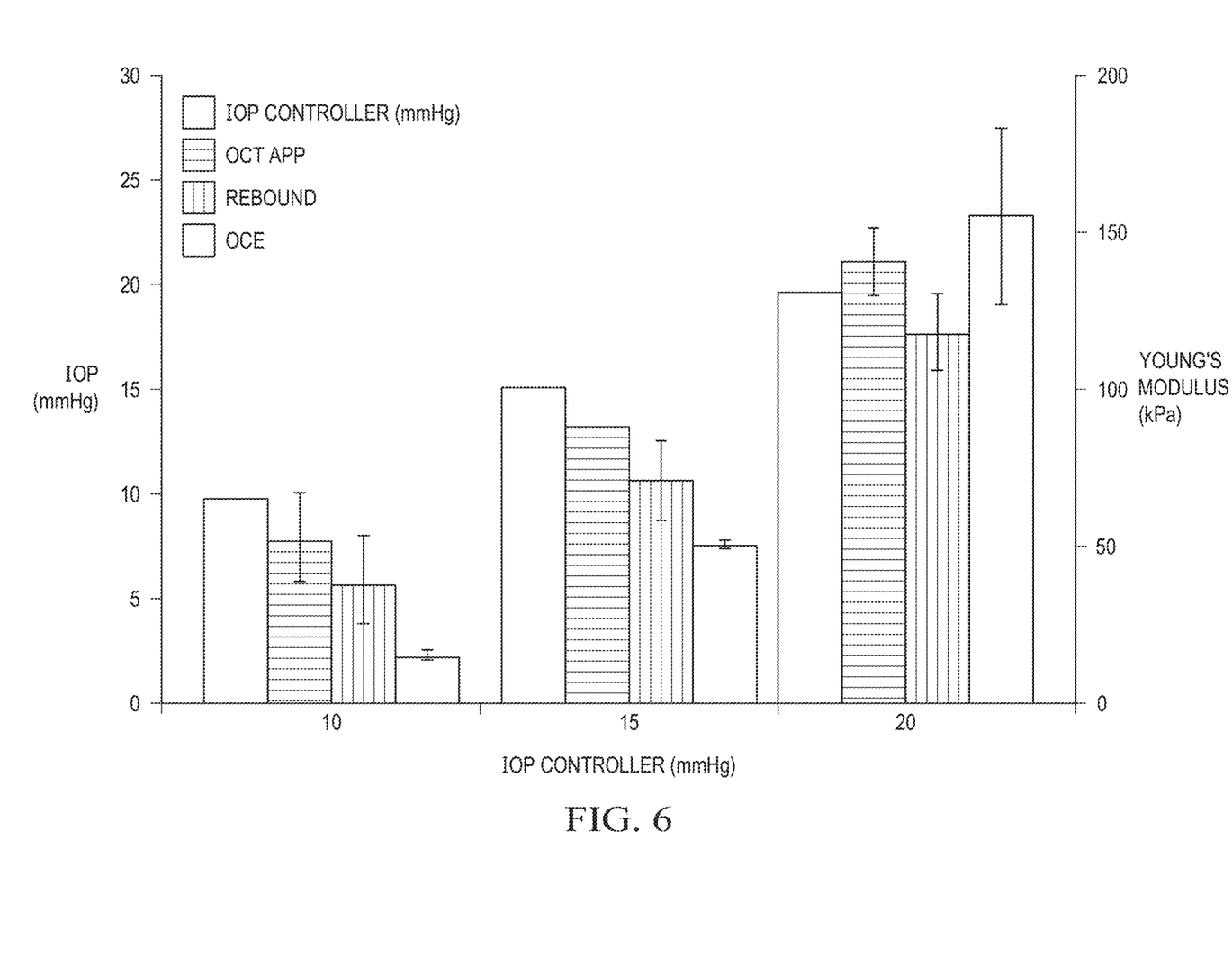
FIG. 6 compares the intraocular pressure as measured by Appl-OCE and by rebound tonometry and includes the Young's modulus quantified by optical coherence elastography. The data are presented as the inter-sample mean±standard deviation of all measurements from three porcine samples for a given artificially controlled intraocular pressure.

The intraocular pressure as measured by Appl-OCE (horizontal stripes) and rebound tonometry (vertical stripes) along with the stiffness of the cornea (right bar) estimated by OCE is shown (FIG. 6). The IOP set by the IOP control system is also plotted for easy comparison. The data are presented as the mean±standard deviation of all measurements from all three samples for a given controlled IOP. Statistical testing by Student's t-test was performed to determine if the measured and controlled IOPs were similar. The results showed that the IOP measured by OCT applanation was not significantly different from the IOP set by the controller, albeit only marginally (P=0.07). However, the IOP, as measured by the rebound tonometer, was significantly different from the IOP as set by the IOP controller (P<0.001). The inter-sample mean±standard deviation of the IOP measurements by both techniques, corneal stiffness, and CCT are presented in Table 1. IOP is measured by a rebound tonometer and Appl-OCE applanation, corneal stiffness is measured by optical corneal elasticity, and CCT was calculated from the OCT structural image, assuming that the cornea had a constant refractive index of 1.376 (23).

TABLE 1

| IOP controller | Rebound Tonometry (mm Hg) | Appl-OCE (mm HG) | Young's Modulus (kPa) | CCT (μm) |
| --- | --- | --- | --- | --- |
| 10 | 5.8 ± 2.5 | 7.8 ± 2.4 | 14.5 ± 2.3 | 1058 ± 97 |
| 15 | 11.1 ± 2.2 | 13.5 ± 0.2 | 50.0 ± 2.0 | 985 ± 86 |
| 20 | 17.7 ± 2.0 | 21.3 ± 2.0 | 158 ± 31.8 | 983 ± 74 |

These results show good correlation with the IOP as set by the artificial IOP control system. Generally, IOP measurements performed by air-puff applanation tend to overestimate IOP (26), however, the OCT applanation results obtained herein slightly underestimated IOP, except at 20 mm Hg, where the IOP was overestimated by 11 mm Hg. The rebound tonometer is known to underestimate IOP (27) which was corroborated herein.

The following references are cited herein.
1. R. Healey, "Screening for glaucoma," in Glaucoma, T. M. Shaarawy et al., Eds., pp. 11-19, Elsevier Saunders, London (2015).
2. Kling et al., PLoS One 9(8), e104904 (2014).
3. Dorronsoro et al., Biomed. Opt. Express 3(3), 473-487 (2012).
4. Roy et al., J. Mech. Behav. Biomed. Mater. 48, 173-182 (2015).
5. Bao et al., Exp. Eye. Res. 137, 11-17 (2015).
6. Li et al., "J. Biomed. Opt. 19(11), 110502 (2014).
7. Asaoka et al., PLoS One 10(10), e0140385 (2015).
8. Bak-Nielsen et al., J. Refract. Surg. 30(6), 408-414 (2014).
9. Gkika et al., Graefes. Arch. Clin. Exp. Ophthalmol. 250(4), 565-573 (2012).
10. Huang et al., Science 254(5035), 1178-1181 (1991).
11. Schmitt, Opt. Express 3(6), 199-211 (1998).
12. Wang and K. V. Larin, J. Biophotonics 8(4), 279-302 (2015).
13. K. V. Larin and D. D. Sampson, Biomed. Opt. Express 8(2), 1172-1202 (2017).
14. Sticker et al., Opt. Lett. 26(8), 518-520 (2001).
15. Wang et al., Appl. Phys. Lett. 89(14), 144103 (2006).
16. Singh et al., Opt. Lett. 40(11), 2588-2591 (2015).
17. Twa et al., Biomed. Opt. Express 5(5), 1419-1427 (2014).
18. Wang et al., Laser Phys. Lett. 10(7), 075605 (2013).
19. Luce, J. Cataract Refract. Surg. 31(1), 156-162 (2005).
20. Ambrosio et al., "Rev. Bras. Oftalmol. 72(2), 99-102 (2013).
21. Song et al., Appl. Phys. Lett. 108(19), 191104 (2016).
22. Song et al., "J. Biomed. Opt. 18(12), 121505 (2013).
23. Mandell, J., Refract. Corneal Surg. 10(2), 125-128 (1994).
24. Singh et al., Biomed. Opt. Express 8(1), 349-366 (2017).
25. J. F. Doyle, Wave Propagation in Structures: Spectral Analysis Using Fast Discrete Fourier Transforms, Springer, New York (1997).
26. Smedowski et al., "Invest. Ophthalmol. Vis. Sci. 55(2), 666-673 (2014).

27. Pereira et al., Vet. Ophthalmol. 14(5), 321-326 (2011).

The present invention is well adapted to attain the ends and advantages mentioned as well as those that are inherent therein. The particular embodiments disclosed above are illustrative only, as the present invention may be modified and practiced in different but equivalent manners apparent to those skilled in the field having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A system for measuring intraocular pressure, ocular tissue geometry and biomechanical properties of an ocular tissue, comprising:
    in one instrument,
        a phase-sensitive swept source optical coherence tomography subsystem, wherein the phase-sensitive swept source optical coherence tomography subsystem comprises optical coherence elastography functionality, a means for delivering a focused micro air-puff to the ocular tissue, and a means for scanning and imaging the ocular tissue with micrometer-scale spatial resolution, subnanometer displacement sensitivity and microsecond-scale temporal resolution; and
        an applanation tonometer subsystem in electronic communication with the phase-sensitive swept source optical coherence tomography subsystem, wherein the applanation tonometer subsystem comprises:
            means for delivering an air-puff to the ocular tissue,
            means for measuring a temporal pressure profile from deformation and applanation of the ocular tissue from the air-puff delivered thereto, and
            means for calculating an intraocular pressure from the temporal pressure profile and spatio-temporally imaged ocular tissue deformation and applanation.

2. The system of claim 1, further comprising:
a housing containing the subsystems;
a computer comprising at least a memory, a processor, a digitizer, a display, and at least one network connection; and
an interface in electronic communication with said subsystems and with the computer.

3. The system of claim 2, wherein the computer is configured to control the subsystems, to process data received from the subsystems, to generate one or more images from processed data, and to display said one or more images.

4. The system of claim 1, wherein the means for scanning the ocular tissue comprises, in electronic communication:
    a scanning laser source configured to operate at about 1260 nm to about 1370 nm;
    a resonant scanner configured to scan a laser beam emitted by the scanning laser source across the ocular tissue; and
    a scanner driver configured to move the resonant scanner over the ocular tissue with operator-configurable scanning distance and phase.

5. The system of claim 1, wherein the means for delivering the air-puff to the ocular tissue comprises, in combination, a rotary solenoid and a plunger configured to deliver the air-puff with a force sufficient to deform the ocular tissue.

6. The system of claim 1, wherein the means for measuring the temporal pressure profile of the ocular tissue is a pressure transducer configured to measure an air-puff pressure at a plurality of time points during deformation and applanation of the ocular tissue.

7. The system of claim 1, wherein the means for calculating the intraocular pressure comprises software configured to correlate the times of applanation of the ocular tissue with a temporal pressure profile and to apply corrections as needed.

8. The system of claim 1, wherein the ocular tissue comprises an in vivo or an ex vivo eye-globe, an in vivo or an ex vivo corneal tissue or an ocular tissue mimic.

9. The system of claim 1, wherein the means for delivering the focused micro air-pulse to the ocular tissue comprises, in electronic communication:
    an air-pulse supply;
    an electronically controlled pneumatic solenoid; and
    an air-pulse controller configured to produce the focused micro air-pulse from the air-pulse supply.

* * * * *

UNITED STATES PATENT AND TRADEMARK OFFICE
CERTIFICATE OF CORRECTION

| | |
|---|---|
| PATENT NO. | : 12,029,492 B2 |
| APPLICATION NO. | : 18/072838 |
| DATED | : July 9, 2024 |
| INVENTOR(S) | : Kirill V. Larin et al. |

It is certified that error appears in the above-identified patent and that said Letters Patent is hereby corrected as shown below:

In the Specification

In Column 1, Lines 13-19, delete "This invention was made with government support under grant numbers 1R01EY022362 and P30EY07551 awarded by the National Institutes of Health. The government has certain rights in the invention.", and insert -- "This invention was made with government support under grant number EY022362 awarded by the National Institutes of Health. The government has certain rights in the invention." --, therefor.

Signed and Sealed this
Twenty-second Day of July, 2025

Coke Morgan Stewart
*Acting Director of the United States Patent and Trademark Office*